(12) United States Patent
Bierhoff et al.

(10) Patent No.: US 11,406,367 B2
(45) Date of Patent: Aug. 9, 2022

(54) SYSTEM WITH PHOTONIC BIOPSY DEVICE FOR OBTAINING PATHOLOGICAL INFORMATION

(71) Applicant: KONINKLIJKE PHILIPS N.V., Eindhoven (NL)

(72) Inventors: Waltherus Cornelis Jozef Bierhoff, Veldhoven (NL); Christian Reich, Eindhoven (NL); Martinus Bernardus Van Der Mark, Best (NL); Bernardus Hendrikus Wilhelmus Hendriks, Eindhoven (NL); Anja Van De Stolpe, Vught (NL); Stephan Voss, Schwerin (DE); Axel Winkel, Zapel-Hof (DE); Marjolein Van Der Voort, Valkenswaard (NL); Vishnu Vardhan Pully, Eindhoven (NL); Gerhardus Wilhelmus Lucassen, Eindhoven (NL); Susanne Dorien Van Den Berg-Dams, Eindhoven (NL); Jarich Willem Spliethoff, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 378 days.

(21) Appl. No.: 16/018,140

(22) Filed: Jun. 26, 2018

(65) Prior Publication Data

US 2018/0303468 A1 Oct. 25, 2018

Related U.S. Application Data

(63) Continuation of application No. 14/436,207, filed as application No. PCT/IB2013/059712 on Oct. 28, 2013, now Pat. No. 10,143,450.

(Continued)

(51) Int. Cl.
*A61B 10/04* (2006.01)
*A61B 5/00* (2006.01)
(Continued)

(52) U.S. Cl.
CPC .......... *A61B 10/04* (2013.01); *A61B 1/00165* (2013.01); *A61B 1/015* (2013.01);
(Continued)

(58) Field of Classification Search
CPC . A61B 10/0096; A61B 10/0275; A61B 10/04; A61B 1/00165; A61B 1/015;
(Continued)

(56) References Cited

U.S. PATENT DOCUMENTS 6,564,087 B1 5/2003 Pitris et al.
7,778,682 B2 8/2010 Kumar et al.
(Continued)

FOREIGN PATENT DOCUMENTS

CN 101984922 A 3/2011
CN 102232852 A 11/2011
(Continued)

OTHER PUBLICATIONS

Nachabe, R. et al., "Estimation of lipid and water concentrations in scattering media with diffuse optical spectroscopy from 900 to 1600nm", J. Biomed. Opt. 15(3), May/Jun., 037015 (2010).
(Continued)

*Primary Examiner* — Michael T Rozanski

(57) ABSTRACT

A biopsy device is provided comprising a tubular member, a hollow shaft and an elongated fiber body. The hollow shaft may have a distal end and a shaft, wherein a laterally (sidewardly) facing notch is formed in the distal portion of the shaft. The elongated fiber body may include at least one optical fiber, preferably at least two optical fibers, with a distal end. The tubular member is movable relative to the (Continued)

shaft, between a first position in which the notch is covered by the tubular member, and a second position in which the notch is not covered by the tubular member. The fiber body is movable within the shaft, between a first position in which the distal end of the optical fiber is located at the distal end of the shaft with the elongated fiber body extending through the notch, and a second position in which the distal end of the at least one optical fiber is located proximally to the notch.

21 Claims, 6 Drawing Sheets

Related U.S. Application Data

(60) Provisional application No. 61/721,541, filed on Nov. 2, 2012.

(51) Int. Cl.
| | |
|---|---|
| *A61B 10/02* | (2006.01) |
| *A61B 5/145* | (2006.01) |
| *A61B 5/1455* | (2006.01) |
| *A61B 5/1459* | (2006.01) |
| *A61B 1/00* | (2006.01) |
| *A61B 1/015* | (2006.01) |
| *A61B 10/00* | (2006.01) |

(52) U.S. Cl.
CPC .......... *A61B 5/0071* (2013.01); *A61B 5/0073* (2013.01); *A61B 5/0075* (2013.01); *A61B 5/0084* (2013.01); *A61B 5/1459* (2013.01); *A61B 5/14503* (2013.01); *A61B 5/14546* (2013.01); *A61B 5/14552* (2013.01); *A61B 5/6848* (2013.01); *A61B 10/0096* (2013.01); *A61B 10/0275* (2013.01); *A61B 5/14556* (2013.01); *A61B 2010/045* (2013.01); *A61B 2560/0475* (2013.01); *A61B 2560/0487* (2013.01)

(58) Field of Classification Search
CPC ...... A61B 2010/045; A61B 2560/0475; A61B 2560/0487; A61B 5/0071; A61B 5/0073; A61B 5/0075; A61B 5/0084; A61B 5/14503; A61B 5/14546; A61B 5/14552; A61B 5/14556; A61B 5/1459; A61B 5/6848
See application file for complete search history.

(56) References Cited

U.S. PATENT DOCUMENTS

| | | | |
|---|---|---|---|
| 7,831,293 | B2 | 11/2010 | Ellis et al. |
| 10,143,450 | B2 * | 12/2018 | Bierhoff ............... A61B 5/0075 |
| 2002/0128570 | A1 | 9/2002 | Bowman et al. |
| 2005/0070818 | A1 | 3/2005 | Mueller |
| 2005/0203419 | A1 | 9/2005 | Ramanujam et al. |
| 2009/0221920 | A1 | 9/2009 | Boppart et al. |
| 2009/0326384 | A1 | 12/2009 | Bigio et al. |
| 2010/0331782 | A1 | 12/2010 | Hendriks et al. |
| 2011/0263922 | A1 | 10/2011 | Dornberger et al. |

FOREIGN PATENT DOCUMENTS

| | | |
|---|---|---|
| JP | H0310255 A | 1/1991 |
| JP | H0638967 A | 2/1994 |
| JP | 2010274123 A | 12/2010 |
| WO | 2011126963 A2 | 10/2011 |

OTHER PUBLICATIONS

Farrell, T.J. et al., "A diffusion theory model of spatially resolved, steady-state diffuse reflectance for the non-invasive determination of tissue optical properties in vivo", Med. Phys. 19 (1992) p. 879-888.

Nachabe, R. et al., "Estimation of biological chromophores using diffuse optical spectroscopy: benefit of extending the UV-VIS wavelength range to include 1000 to 1600 nm", Optics Express, vol. 18, 2010, pp. 1432-1442.

Zhang, Q., et al. "Turbidity-free fluorescence spectroscopy of biological tissue", Opt. Lett., 2000 25(19), p. 1451-1453.

Nachabe, R. et al., "Effect of bile absorption coefficients on the estimation of liver tissue optical properties and related implications in discriminating healthy and tumorous samples," Biomedical optics express, vol. 2, 2011, pp. 600-614.

Palero, J.A. et al. , "In vivo nonlinear spectral imaging microscopy of visible and ultraviolet irradiated hairless mouse skin tissues", Photochem. Photobiol. Sci., 2008, 7, 1422-1425.

Hendriks, B.J.W. et al., High-resolution resonant and nonresonant fiber-scanning confocal microscope, J. Biomed. Opt. 16(2011) pp. 026007.

Gerweck, L.E. et al. "Cellular pH Gradient in Tumor versus Normal Tissue: Potential Exploitation for the Treatment of Cancer", Cancer Research 56, 1194-1198, Mar. 15, 1996.

* cited by examiner

SYSTEM WITH PHOTONIC BIOPSY DEVICE FOR OBTAINING PATHOLOGICAL INFORMATION

CROSS REFERENCE TO RELATED APPLICATION

This is a continuation of prior application Ser. No. 14/436,207, filed Apr. 16, 2015. Application Ser. No. 14/436,207, and issued as U.S. Pat. No. 10,143,450 on Dec. 4, 2018, which is the U.S. National Phase application under 35 U.S.C. § 371 of International Application Serial No. PCT/IB2013/059712, filed on Oct. 28, 2013, which claims the benefit of U.S. Application Ser. No. 61/721,541, filed on Nov. 2, 2012. These applications are hereby incorporated by reference herein.

FIELD OF THE INVENTION

The invention generally relates to a system including facilities for in-vivo and for ex-vivo tissue inspection. Particularly, the invention relates to a system including a biopsy device with optical fibers and a lateral notch for in-vivo tissue inspection and for taking a biopsy which may additionally be subjected to ex-vivo tissue inspection.

BACKGROUND OF THE INVENTION

Traditional pathology makes use of ex-vivo analysed tissue samples. As a result some of the relevant information of the in-vivo tissue state, e.g. its metabolic state, is lost in this process and cannot be measured on the tissue slide used for histopathology diagnostics. Biopsies are typically performed by surgeons or interventional radiologists, and subsequently examined by a pathologist. An exemplary workflow for obtaining a biopsy is depicted in FIG. 1. For positioning the biopsy device (usually a needle with a shaft 100 having a lateral recess 200, and an outer tubular member 500) accurately in the suspicious tissue, the correct location is commonly determined using image guidance such as Ultrasound or X-ray. While imaging may provide coarse guidance of the needle towards the region of interest, it is often challenging to precisely identify the boundaries of small lesions or tumors with the biopsy needle using standard imaging modalities. As a consequence, biopsies are often taken at the wrong location, which increases the risk of false diagnoses. An additional challenge is the heterogeneity present in many tumors where for example multiple biopsies in different regions of the tumor are required, and this requires more accurate positioning in different parts of the tumor tissue. The association between biopsy location and subsequent biopsy histopathology analysis is important to assess the heterogeneity and the optimal (targeted) therapy to choose. This is becoming more important with the increasing use of neoadjuvant cancer therapy, prior to surgery, e.g. in breast cancer.

There are various imaging devices that provide in-vivo information such as functional MRI imaging and PET-CT imaging. Due to the above described difficulties, it is difficult to link information obtained by these imaging modalities to histopathology results from a biopsy slide taken from the body because the link to the exact position of the biopsy is difficult, in part because of limited resolution of the imaging modalities.

In order to position a biopsy needle under image guidance more accurately in the suspicious tissue, tissue sensing at the tip of the device may be required. Current biopsy needles often do not have such tissue feedback possibilities. Recently, elongated interventional devices have been reported with optical fibers integrated into the device which provide feedback from the tissue at the tip of the device. Such devices allow for fine-guidance towards small volumes of suspicious tissue, in particular for tissue which does not show sufficient contrast in imaging. In order to allow tissue discrimination, these devices employ diffuse reflectance spectroscopy (DRS). For DRS, such devices should be designed with the maximum possible distance between the source and detector fibers to ensure an optimal tissue characterization.

SUMMARY OF THE INVENTION

Whereas tissue sensing at the tip can ensure that the device is correctly positioned at the location of interest, it is desirable that the biopsy is obtained from exactly the same location. For this, a special design is required to ensure that the correct tissue sample is captured in the notch of a biopsy device. During tissue measurements, the notch of the biopsy device is at a different location than the position of the fiber ends at the tip of the device. A special construction is required such that when the biopsy is taken after the tissue sensing is completed, the notch of the biopsy device is positioned at the location where the final tissue sensing took place.

For biopsy devices with a lateral notch, the presence of the notch sets strict constraints for integrating the optical fibers within the device. Consequently, the fibers would be confined to the lower part of the shaft of the device, resulting in a small and likely insufficient source-detector fiber distance at the tip.

A biopsy device may consist of several moveable parts, which in the case of a fully-automated biopsy gun are ejected at high speeds with abrupt movements. Accordingly, the optical fibers need to be integrated in a way which ensures their mechanical stability and which does not restrict the usability of the biopsy gun.

Further, the typical workflow for obtaining a biopsy should not be changed.

It may be seen as an object to integrate optical fibers at the tip of a biopsy device (needle) in such a way that (1) the obtained tissue sample (biopsy) is the same as the tissue investigated by optical fibers prior to taking the biopsy, (2) a sufficient source-detector fiber distance can be realized for tissue characterization, and (3) that the modifications do not require a change in the clinical workflow of a standard biopsy procedure. It may be seen as a further object to combine in-vivo information, for example metabolic information to the standard histopathology to obtain an advanced pathology data set, integrating conventional pathology staining results with such information on an individual cellular level, and to provide more complete information on the biological characteristics and behaviour of the cells, relevant for improved diagnostics (including therapy response monitoring).

In other words: it is an object of the invention to provide system and method for obtaining in-vivo and ex-vivo pathological information of a single tissue sample, i.e. the same tissue sample. This and further objects are solved by the subject-matter of the independent claim. Further embodiments are described in the dependent claims.

The invention proposes an integrated solution for adding tissue sensing at the tip of a biopsy device. The biopsy device consists of the optical sensing part at the tip of the device and a shaft with a lateral notch characterized in that the position of optical sensing part before taking the biopsy and the proximal position of the notch when taking the biopsy are substantially the same. Hence when the shaft is pushed forward (as in FIG. 3B) the notch will fill with tissue that had been sensed in FIG. 3A.

Generally, a system according to an embodiment may comprise a biopsy device with a tubular member, a hollow shaft and an elongated fiber body. The hollow shaft may have a distal end and a shaft portion adjacent the distal end, wherein a laterally (sidewardly) facing notch is formed in that portion of the shaft. The elongated fiber body may include at least one optical fiber, preferably at least two optical fibers, with a distal end.

The fiber body may be movably accommodated within the hollow shaft, and the shaft may be movably accommodated within the tubular member, wherein the tubular member is movable between a first position in which the notch is covered by the tubular member, and a second position in which the notch is not covered by the tubular member, and wherein the fiber body is movable between a first position in which the distal end of the optical fiber is located at the distal end of the shaft with the elongated fiber body extending through the notch, and a second position in which the distal end of the at least one optical fiber is located proximally to the notch.

Accordingly, the shaft of a biopsy device is formed as a hollow shaft that provides space for inserting an elongated body with integrated optical fibers. During device (needle) positioning, the full volume of the shaft, including the notch, is now occupied by the fiber body and allows for guiding the optical fibers to the tip with a sufficiently large source-detector fiber distance to ensure an accurate tissue characterization.

When the biopsy is taken, the fiber body is released from the shaft and the full volume of the notch becomes available for securing the biopsy. Thus, the use within the clinical workflow remains essentially the same as for a conventional biopsy needle, except the added tissue sensing functionality during needle positioning.

According to an embodiment, the fiber body comprises a bevel at a distal end of the fiber body, wherein the distal end of the at least one optical fiber is located at the bevel of the fiber body, wherein a smooth surface is formed by the front surface of the optical fiber and the surface of the bevel. Alternatively, the distal end of the at least one optical fiber may protrude beyond the bevel of the fiber body. Alternatively, the distal end of at least one optical fiber may be located inside the fiber body adjacent the bevel. Furthermore, the front surface of the optical fiber may have a different angle than the bevel of the fiber body.

A 'bevel' is a geometrical structure allowing for introducing the needle into tissue. Usually, a shaft of a needle includes a circular cross section. The distal end of a needle shaft is cut such that an oval surface is formed, which is inclined relative to the longitudinal axis of the shaft. The bevel forms a pointed tip at the most distal end of the needle. It should be noted that the bevel might form an acute angle with the shaft, such that the needle includes a pointed tip. Preferably, the acute angle might be approximately 20°.

According to an embodiment, the bevel of the fiber body together with the slanted surface of the distal end of the hollow shaft may form the geometrical structure allowing for introduction of the device into tissue.

In the following, geometrical aspects will be defined for a better understanding. First of all, the device includes a longitudinal main axis, usually the centre axis of a rotationally symmetrical shaft. Further, the tip portion of the device is cut at an angle to the main axis forming the bevel. The pointed tip of the bevel is directed to the 'front' of the needle. As a result, looking from the 'side', it is possible to recognize the angle between the bevel and the main axis, and further it is possible to look onto and into a recess formed at the side, i.e. laterally.

It should be noted that the end surface of a fiber at the opening in the bevel may have a circular shape or an oval shape in case of a substantially circular cross section of the fiber. Depending on the angle at which the fiber will end at the bevel surface, the shape of the end surface of the fiber will be effected and therefore also the direction of the emitted or received light.

The fiber body has an outer diameter, and the end surfaces of the fibers are arranged within the body at a distance to each other. Preferably, the distance between the fiber ends is greater than the diameter of the body. For example, the distance is more than 1.1 times greater than the diameter. Particularly, the distance may be more than 1.25 times greater than the diameter. Preferably, the distance may be more than 1.5 times greater than the diameter. In other words, the distance between the fiber ends should be as great as possible. Such distances are measured from the central axis of one of the fibers to the central axis of the other one of the fibers.

It will be understood that the tubular member may include a sharpened distal edge.

According to a further embodiment, an insert may be arranged within the hollow shaft between the distal end of the hollow shaft and the notch, wherein the insert may include openings for accommodating the distal end of the at least one optical fiber, when the fiber body is in the first position, i.e. when the fiber body is in a position in which the distal end of the optical fiber(s) is located at the distal end of the shaft with the elongated fiber body extending through the notch.

According to another embodiment, the biopsy device may further comprise a channel for injecting or extracting a fluid. Such a channel may be an additional channel formed in the fiber body and extending through that body in a longitudinal direction, but may also be formed in the wall of the shaft or between the fiber body and the shaft or between the shaft and the outer tubular member.

According to a further embodiment, the biopsy device may further comprise a tissue retraction channel, wherein a suction device may apply vacuum to the channel for retracting a sample of tissue. For example, the channel in which the fiber body is accommodated within the shaft, may be used for retracting a sample, after removing the fiber body. Alternatively, the channel may be formed in the fiber body between optical fibers which are preferably arranged as much as possible at opposite sides of the elongated body.

According to another embodiment, the biopsy device further comprises a console including a light source, a light detector and a processing unit for processing the signals provided by the light detector, wherein one of the light source and the light detector may provide wavelength selectivity. The light source may be one of a laser, a light-emitting diode or a filtered light source, and the console may further comprise one of a fiber switch, a beam splitter or a dichroic beam combiner. Furthermore, the device may be adapted to perform at least one out of the group consisting of diffuse reflectance spectroscopy, diffuse optical tomography, differential path length spectroscopy, and Raman spectroscopy.

The system may further comprise a device adapted for ex-vivo tissue inspection, and/or a storage container for receiving an extracted tissue sample and for storing pathology information obtained by an in-vivo tissue inspection and/or an ex-vivo tissue inspection.

According to another aspect, a method for obtaining pathological information regarding a tissue sample is provided, the method generally comprising the steps of obtaining information from an in-vivo tissue inspection, obtaining information from an ex-vivo tissue inspection, wherein the same tissue sample is inspected firstly in-vivo and then ex-vivo.

The in-vivo tissue inspection may include at least one out of the group consisting of diffuse reflectance spectroscopy, diffuse optical tomography, differential path length spectroscopy, and Raman spectroscopy. On the other hand, the ex-vivo tissue inspection may include at least one of making tissue slices, staining by Hematoxylin and eosin (H&E) and/or a specific biomarker, and optically scanning.

According to an embodiment, the method may further comprise the step of integrating the information obtained by in-vivo tissue inspection and the information obtained by ex-vivo tissue inspection. For example, the in-vivo obtained information may be used for an interpretation of the ex-vivo obtained information.

The method may further comprise the step of storing the pathology information of the tissue sample, obtained by the in-vivo tissue inspection and/or by the ex-vivo tissue inspection, by a storage containing which may also be adapted to receive a tissue sample.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

Figure 1:
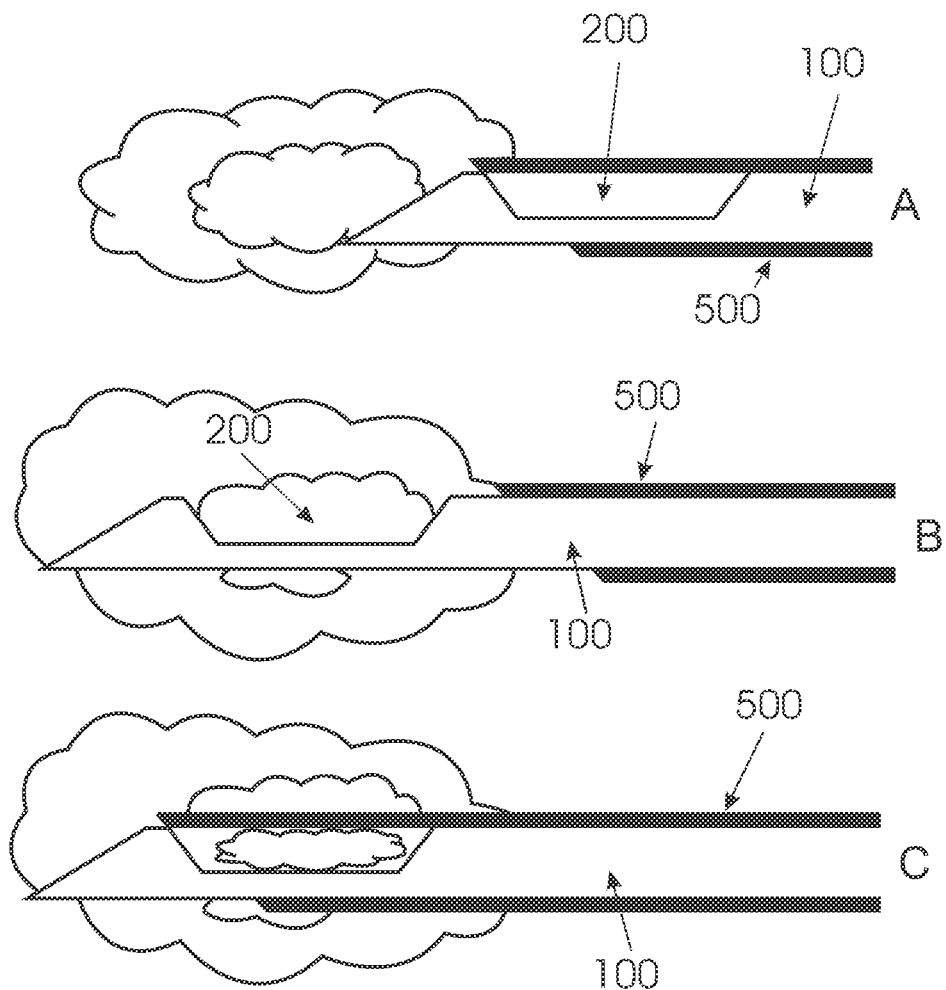
FIG. 1 is an illustration of taking a biopsy with a known needle.
Figure 2:
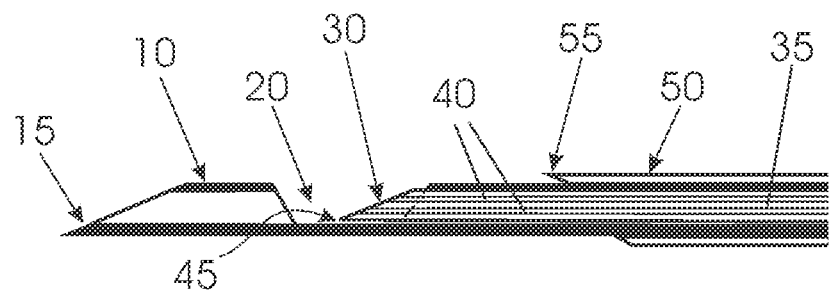
FIG. 2 shows a biopsy device according to a first embodiment.

In FIG. 2, a first embodiment of a biopsy device is shown, having a hollow shaft 10, fiber body 35 and an outer tubular member 50. The hollow shaft 10 includes a distal end or tip 15 forming a slanted surface, wherein the slanted surface may have an oval shape in case the hollow shaft has a circular cross section. Furthermore, a lateral recess or notch 20 is formed in the shaft, wherein the notch 20 is substantially formed by a lateral opening and a section of the bore extending through the shaft in a longitudinal direction.

The fiber body 35 is formed by an elongated and solid element in which channels for accommodating optical fibers 40 are provided. The fiber body includes a bevel 30 at the distal end thereof. The outer tubular member 50 comprises a sharpened distal edge 55. For a better visualization, the fiber body is in FIG. 2 in an intermediate position with the bevel 30 within the notch 20.

For a better visualization, the fiber body is in FIG. 2 in an intermediate position with the bevel 30 within the notch 20.

For tissue sensing, an optical fiber 40 for illumination and collecting light is required with distal end at the tip 15 of the biopsy device. The proximal end of the fiber may be connected to an optical console capable of sending and receiving light.

For optimal tissue sensing, it is required to guide at least two optical fibers 40 (source and detector) towards the device tip 15, and the fiber tip ends should have a maximized distance from each other. According to the first embodiment, this is achieved by a hollow shaft providing space for inserting a fiber body 35 with optical fibers 40 integrated at a sufficient source-detector fiber distance at the tip, i.e. at the bevel 30.

Figure 3:
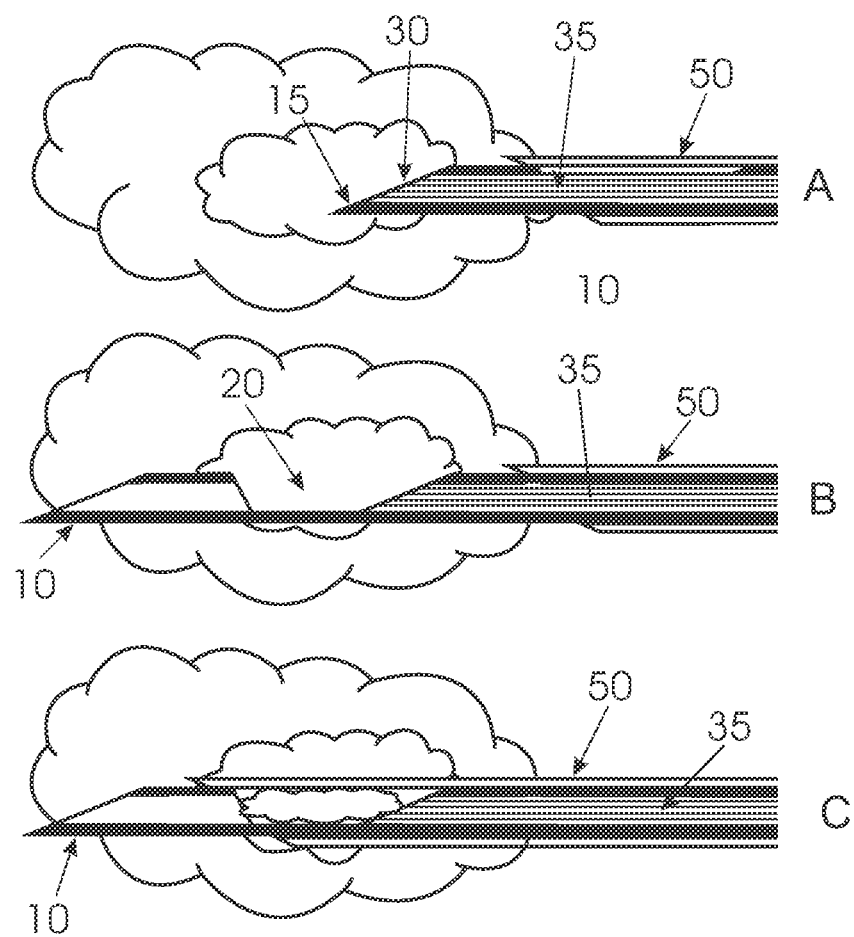
FIG. 3 illustrates steps of taking a biopsy with a device of FIG. 2.

In a typical clinical workflow shown in steps A-C of FIG. 3, the biopsy device is inserted into the patient with the outer tubular member 50 (the cutting cannula) covering the notch 20 of the shaft 10 to ensure a smooth protrusion (step A in FIG. 3). Hence the notch 20 is not exposed to the tissue in this step, and the hollow space in the shaft 10 (including the notch 20) can be occupied by the fiber body without altering the workflow. The proposed solution allows for additional tissue characterization at the tip during needle positioning.

At the target location, the shaft 10 is ejected whereas the fiber body 35 remains in its position (step B in FIG. 3). Thereby, the notch 20 is no longer occupied by the tubular member 50 and the biopsy can be obtained in a conventional way (step C in FIG. 3).

Whereas the hollow shaft 10 and the tubular member 50 are moveable parts, the fiber body may remain at a fixed position during the entire procedure. Since the fiber body 35 with the integrated optical fibers 40 is not moved, the design is compatible with fast (fully-automated) shooting mechanisms, where the workflow steps B and C are successively executed at high speed. Thus, the risk of damaging the optical fibers 40 by strong mechanical forces can be circumvented.

The length and position of the shaft 10 may be chosen in such a way that the fiber body 35 is facing the proximal side of the notch 20 when exposed after the ejection (step B). This allows for a direct characterization of the tissue present in the notch 20, just before the biopsy is taken (step C). With this option, a confirmation measurement from the tissue in the notch can be performed in-situ, and an optimal correlation between the biopsy sample and the optical measurement can be ensured. This is particularly useful for biopsy devices with a manual or semi-automated shooting mechanism, where the workflow steps 2 and 3 can be executed with a user-defined time delay to allow for additional tissue measurements in the notch.

Figure 4:
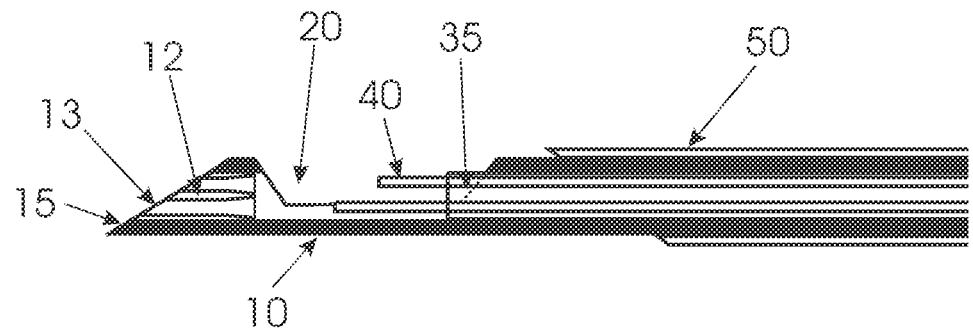
FIG. 4 shows a biopsy device according to a second embodiment.

FIG. 4 shows a second embodiment of a biopsy device which differs from the first embodiment (FIG. 2) in that an insert 12 is inserted in the portion of the hollow shaft 10 between the distal end 15 and the notch 20. The insert 12 may be a small fixed element at the tip by means of which the tip of the hollow shaft 10 may be closed during biopsy. For a better visualization, the fiber body 35 is in FIG. 4 in an intermediate position with the protruding ends of the optical fibers 40 within the notch 20.

Figure 5:
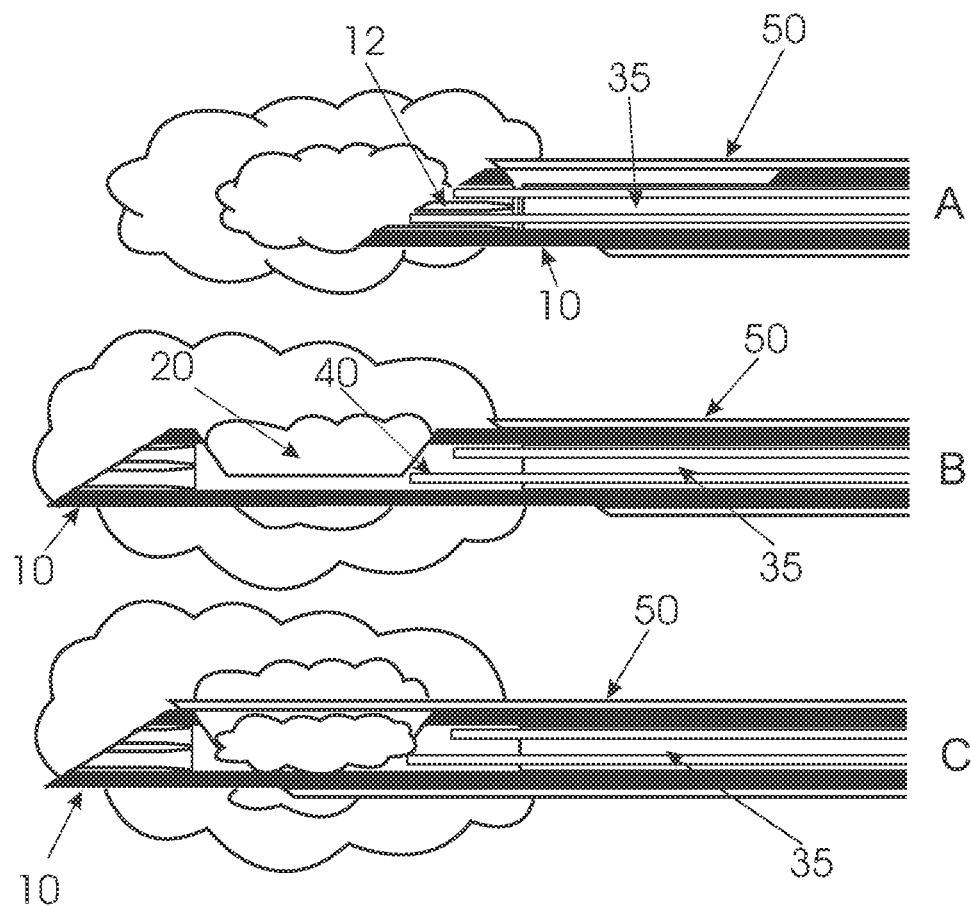
FIG. 5 illustrates steps of taking a biopsy with a device of FIG. 4.

Similar to steps A-C of FIG. 3, steps A-C of FIG. 5 show a clinical workflow where the biopsy device shown in FIG. 4 is inserted into the patient with the outer tubular member 50 (the cutting cannula) covering the notch 20 of the shaft 10 (step A in FIG. 5). During ejection of the shaft 10, tissue may enter the hollow tip portion of the shaft and may be cut by the protruding shaft with the hole (step B in FIG. 5). An insert 12 may ensure that the amount of tissue being cut is only the absolute minimum that is medically required for obtaining a proper biopsy. As in step C of FIG. 3, biopsy can be obtained as shown in step C in FIG. 5.

The insert 12 has two or more (conical) openings/channels 13 which are just large enough (typically some 100 μm) for loosely guiding the optical fibers 40 towards the tip 15 of the shaft 10. The fiber body 35 is adapted accordingly, so that the optical fibers 40 protrude a well-defined extent out of the body to fit into the guiding channels 13 of the insert 12. Preferably, the dimensions of the insert are minimized (some millimetres only) to reduce the required protrusion length of the optical fibers 40 from the body of the fiber body 35.

Furthermore, a small opening for applying vacuum can be realized within the shaft or in the fiber body, and it may be used for sucking tissue into the notch 20 after the shaft 10 has been ejected (step B) to ensure that the biopsy is of sufficient size. By way of this, the underpressure may ensure that the tissue is brought in close contact with the optical fibers 40 facing the proximal side of the exposed notch 20, for the case that the tissue in the notch is characterized prior to obtaining the biopsy.

Such an opening 45 is schematically illustrated in FIG. 2, wherein this opening may be formed within the shaft 10, within the fiber body 35, but also as a gap between the shaft 10 and the fiber body 35.

The incorporation of a small opening for applying underpressure can also allow for simultaneous biological/physiological analysis of the blood/tissue under consideration, thus obtaining a better biopsy quality. The underpressure can be used to suck in small amounts (microliter) of body fluid (for instance blood/serum, bile, or else) for instant biochemical analysis, which can be used to complement the optical tissue characterization.

For this, the underpressure is preferably realized by a small vacuum opening within the fiber body, so that the blood sampling can be performed within the described design at the tip (workflow step A in FIG. 3) and also in the notch (step B in FIG. 3). The absorbed blood/cells could be analyzed by appropriate detectors (such as chip-sized microfluidic devices and/or MEMS) connected to the distal end of the vacuum channel, thereby enabling instantaneous analysis.

For instance, MEMS-based pH sensors could allow for complementary classification of tumor (acidic) vs. normal (basic) tissue based on pH. Apart from pH sensors, also other specific sensors may be used that could characterize the tissue sample in consideration. This could serve as complimentary means to support the optical tissue sensing in difficult cases, and thereby improve the results of photonic biopsy procedures even further.

It is noted that the 'bevel' might also have another shape or structure at the tip of the device, useful for introducing the device into a tissue. For example, the bevel might be a convex or concave surface, or the bevel might be a combination of several small surfaces, wherein these surfaces are connected to each other by steps or edges. It might also be possible that the cross section of the shaft is not completely cut by the bevel, such that an area remains which is blunt, i.e. is for example perpendicularly orientated relative to the longitudinal axis of the shaft. Such a 'blunt' end might include rounded edges or might also form a rounded leading edge. As another example, a sharp edge might be formed by two or more slanted surfaces being symmetrically or asymmetrically arranged to form the tip of the device.

Figure 6:
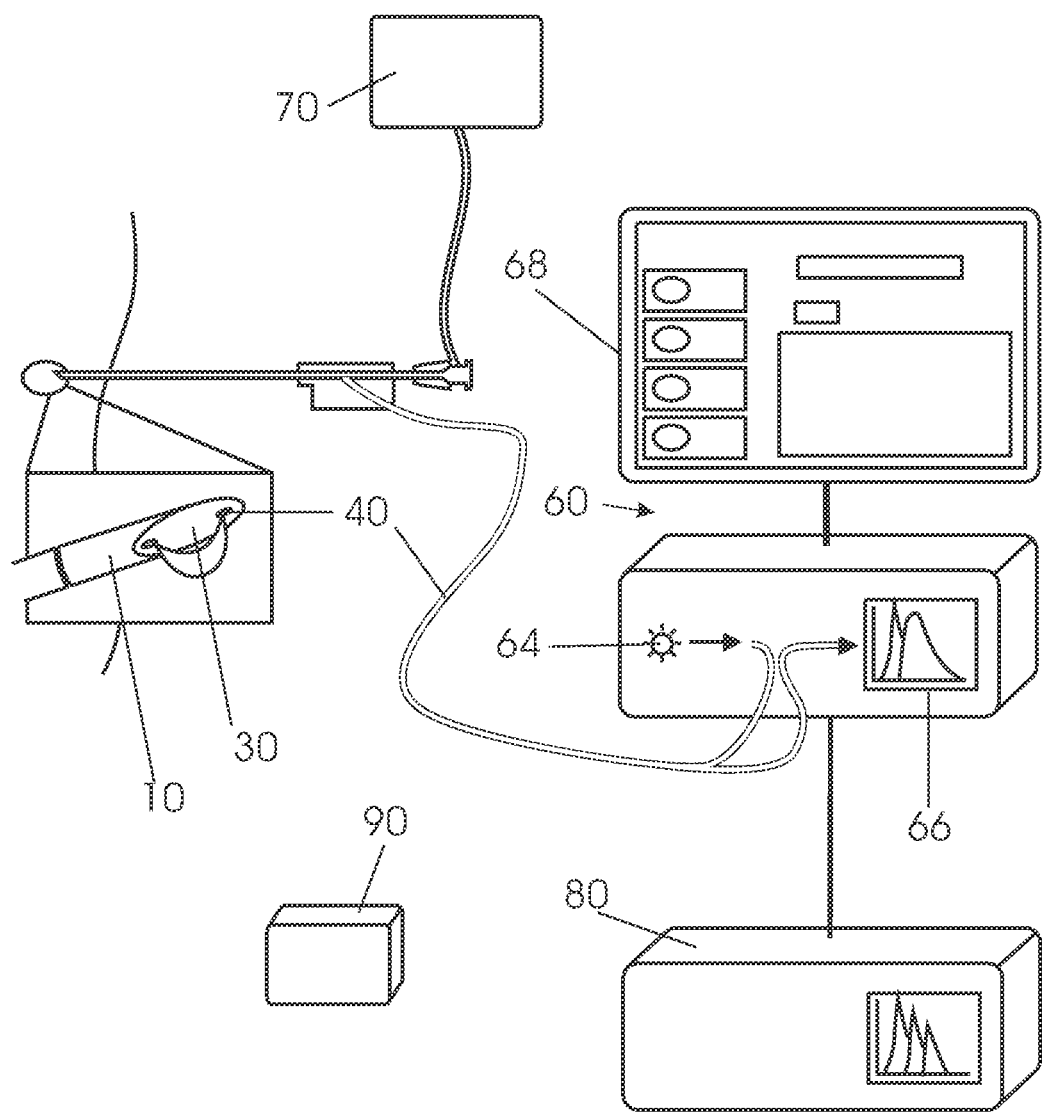
FIG. 6 shows a system including a biopsy device and a console.

As shown in FIG. 6, the fibers 40 of the interventional device are connected to an optical console 60. The optical fibers can be understood as light guides or optical waveguides. In an embodiment, the console 60 comprises a light source 64 in the form of a halogen broadband light source with an embedded shutter, and an optical detector 66. The optical detector 66 can resolve light with a wavelength substantially in the visible and infrared regions of the wavelength spectrum, such as from 400 nm to 1700 nm. The combination of light source 64 and detector 66 allows for diffuse reflectance measurements. For a detailed discussion on diffuse reflectance measurements see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

Optionally it is also possible that the console is couple to an imaging modality capable of imaging the interior of the body, for instance when the biopsy is taken under image guidance. In this case it is also possible to store the image of the interior when the biopsy is taken to a container of the biopsy. In this case the in-vivo information of the optical biopsy needle, the information of the pathology of the biopsy as well as the location where the biopsy was taken are brought together for advanced pathology.

On the other hand, also other optical methods can be envisioned like diffuse optical tomography by employing a plurality of optical fibers, differential path length spectroscopy, fluorescence and Raman spectroscopy to extract tissue properties.

Further shown in FIG. 6 are a suction device 70, a device 80 for obtaining ex-vivo pathology information, and a storage container 90. The suction device may be connected to a proximal end of the biopsy device, such that underpressure or a vacuum can be applied through the biopsy device to the distal end of the same, in particular to the notch at the distal end of the biopsy device.

The device 80 may be connected to the console 60 by means of a wire or wireless, for interchanging information like control commands or data representing pathological aspects of an inspected tissue sample. The device 80 may be a digital pathology systems consisting of an optical scanner and an image management system to enable digitizing, storage, retrieval, and processing of tissue staining images, reading the information stored in the storage box container, and integrating this information with the digitized staining data set, to be presented to the pathologist. In addition to this, the data set from the photonic biopsy device may be either presented next to the histopathology image or the two data sets may be fused in the image, characterized and recognizable by a certain coloring pattern of the image. For instance the oxygenation level measured in-vivo could be added as a red color, where deep red means low oxygenation and bright red would mean high oxygenation level. Additionally, molecular spatial distributions from FTIR or Raman could be added as a color coded mapping to the pathology slide of specific molecules.

The tissue sample, which may firstly be subjected to an in-vivo tissue inspection, i.e. an inspection within a living body, and which may secondly subjected to an ex-vivo tissue inspection by means of the device 80, may be situated in the container 90. Molecular diagnostics can also be performed on the tissue biopsy (e.g. sequencing or PCR), or part of the biopsy.

The storage container for the biopsy may further be such that the optical information obtained in-vivo and/or ex-vivo can be stored on it. This can be a barcode label which can be read at the pathology department by the digital pathology device. It can also be a micro chip where the optical information can be stored electronically. Instead of storing the actual information it is also possible to store an "address" or "link" of where the information may be retrieved.

According to another embodiment, the container 90 may be placed in the console 60. The data can then be written on the container while the photonic biopsy device is attached to the console. The data can be written in the form of a barcode or can electronically be stored in the chip on the container.

A processor transforms the measured spectrum into physiological parameters that are indicative for the tissue state and a monitor 68 may be used to visualize the results.

A computer program executable on the processor may be provided on a suitable medium such as an optical storage medium or a solid-state medium supplied together with or as part of the processor, but may also be distributed in other forms, such as via the Internet or other wired or wireless telecommunication systems.

For fluorescence measurements the console must be capable of providing excitation light to at least one source fiber while detecting tissue-generated fluorescence through one or more detection fibers. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fiber as the light for diffuse reflectance. This may be accomplished by, e.g., using a fiber switch, or a beam splitter or dichroic beam combiner with focusing optics. Alternatively, separate fibers may be used for providing fluorescence excitation light and light for diffuse reflectance measurements.

To perform spectroscopy, the acquired spectra may be fitted using a custom made Matlab 7.9.0 (Mathworks, Natick, Mass.) algorithm. In this algorithm, a widely accepted analytical model was implemented, namely the model introduced by the reference T. J. Farrel, M. S. Patterson and B. C. Wilson, "A diffusion theory model of spatially resolved, steady-state diffuse reflectance for the non-invasive determination of tissue optical properties". Med. Phys. 19 (1992) p. 879-888, which is hereby incorporated by reference in entirety. The input arguments for the model of this reference are the absorption coefficient $\mu_a(\lambda)$, the reduced scattering coefficient $\mu'_s(\lambda)$ and the center-to-center distance between the emitting and collecting fibers at the tip of the probe.

In the following part, the model will be explained briefly. The used formulas are mainly based on work of Nachabé et al., and reference is thus made to R. Nachabe, B. H. W. Hendriks. M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442, which is hereby incorporated by reference in entirety, and furthermore reference is made to R. Nachabe. B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010), which is also hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter a corresponds to the reduced scattering amplitude at this specific wavelength.

$$\mu_s(\lambda) = a\left(\rho_{MR}\left(\frac{\lambda}{\lambda_0}\right)^{-b} + (1-\rho_{MR})\left(\frac{\lambda}{\lambda_0}\right)^{-4}\right) [cm^{-1}] \quad (Eq. 1)$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size. For a homogeneous distribution of absorbers, the total light absorption coefficient $\mu_a(\lambda)$ can be computed as products of the extinction coefficients and volume fraction of the absorbers (see FIG. 8)

$$\mu_a^{Total} = f_1\mu_a^1 + f_2\mu_a^2 + f_3\mu_a^3 + \ldots \quad (Eq. 2)$$

Instead of modeling the absorption coefficient $\mu_a(\lambda)$ as the sum of absorption coefficients weighted by the respective concentrations of the four chromophores of interest, it was decided to express the tissue absorption coefficient as $$\mu_a^{Tissue}(\lambda) = C(\lambda)v_{Blood}\mu_a^{Blood}(\lambda) + v_{WL}\mu_a^{WL}(\lambda) [cm^{-1}] \quad (Eq. 3)$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL}=[Lipid]+[H_2O]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1-\exp(-2R\mu_a^{Blood}(\lambda))}{2R\mu_a^{Blood}(\lambda)} \quad (Eq. 4)$$

where R denotes the average vessel radius expressed in cm. The absorption coefficient related to blood is given by $$\mu_a^{Blood}(\lambda)=\alpha_{BL}\mu_a^{HbO_2}(\lambda)+(1-\alpha_{BL})\mu_a^{Hb}(\lambda) \text{ [cm}^{-1}\text{]} \quad \text{(Eq. 5)}$$

where $\mu_a^{HbO_2}(\lambda)$ and $\mu_a^{Hb}(\lambda)$ represent the basic extinction coefficient spectra of oxygenated hemoglobin HbO$_2$ and deoxygenated hemoglobin Hb, respectively. The oxygenated hemoglobin fraction in the total amount of hemoglobin is noted $\alpha_{BL}$=[HbO$_2$]/([HbO$_2$]+[Hb]) and is commonly known as the blood oxygen saturation. The absorption due to the presence of water and lipid in the measured tissue is defined as $$\mu_a^{WL}(\lambda)=\alpha_{WL}\mu_a^{Lipid}(\lambda)+(1-\alpha_{WL})\mu_a^{H_2O}(\lambda) \text{ [cm}^{-1}\text{]} \quad \text{(Eq. 6)}$$

In this case the concentration of lipid related to the total concentration of lipid and water together can be written as $\alpha_{WF}$=[Lipid]/([Lipid]+[H$_2$O]), where [Lipid] and [H$_2$O] correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf. the reference R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442. For further explanation and validation of this theorem reference is made to the reference R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For example by means of the described algorithm optical tissue properties may be derived such as the scattering coefficient and absorption coefficient of different tissue chromophores: e.g. hemoglobin, oxygenated haemoglobin, water, fat etc. These properties are different between normal healthy tissue and diseased (cancerous) tissue.

Figure 8:
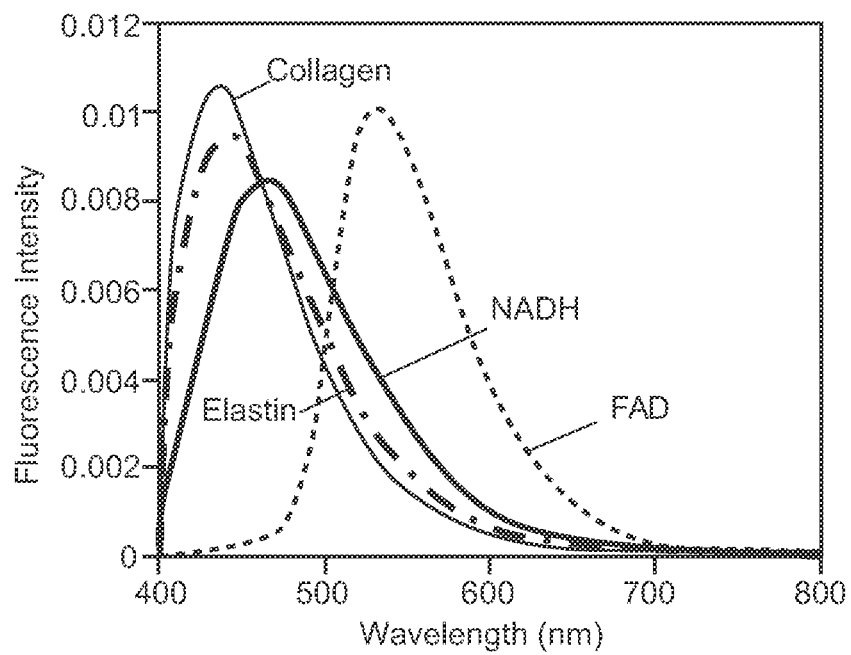
FIG. 8 shows fluorescence curves for collagen, elastin, NADH and FAD.

The main absorbing constituents in normal tissue dominating the absorption in the visible and near-infrared range are blood (i.e. hemoglobin), water and fat. In FIG. 8 the absorption coefficient of these chromophores as a function of the wavelength are presented. Note that blood dominates the absorption in the visible range, while water and fat dominate in the near infrared range.

Figure 7:
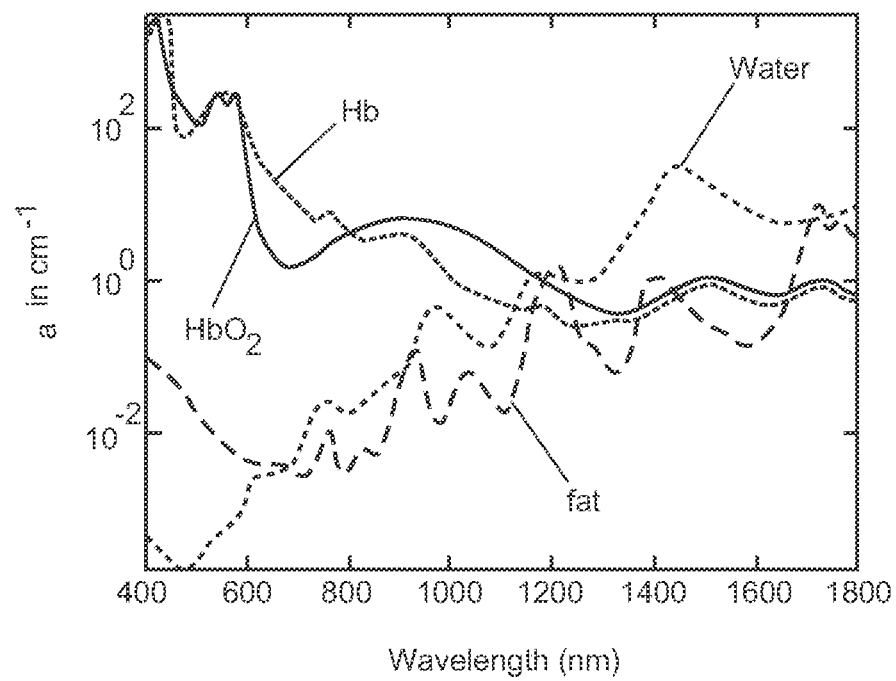
FIG. 7 shows a log plot of absorption coefficient of blood, water and fat.

The total absorption coefficient is a linear combination of the absorption coefficients of for instance blood, water and fat (hence for each component the value of that shown in FIG. 7 multiplied by its volume fraction). By fitting the model to the measurement while using the power law for scattering, the volume fractions of the blood, water and fat as well as the scattering coefficient may be determined.

Another way to discriminate differences in spectra is by making use of a principal components analysis. This method allows classification of differences in spectra and thus allows discrimination between tissues. Apart from diffuse reflectance also fluorescence may be measured. Then for instance parameters like collagen, elastin, NADH and FAD could be measured too (see FIG. 8). Especially, the ratio NADH/FAD, which is called the optical redox parameter, is of interest because it is an indicator for the metabolic state of the tissue, as described in Zhang Q., et al. "Turbidity-free fluorescence spectroscopy of biological tissue", Opt. Lett., 2000 25(19), p. 1451-1453, which is changed in cancer cells and assumed to change upon effective treatment of cancer cells.

It is also possible to detect the response of the body to exogenous fluorophores that can be detected by the optical biopsy device. Furthermore, these could also be linked to measurements of the exogenous fluorophores by imaging modalities like optical mammography based on diffuse optical imaging.

The described devices can be used in minimally invasive needle interventions such as low-back pain interventions or taking biopsies in the field of cancer diagnosis or in case where tissue characterization around the needle is required.

In the following, exemplary needle devices will be described with respect to their outer diameter, their insertion length, and their preferred use.

A biopsy needle might have an outer diameter of 1.27 mm up to 2.108 mm, might be inserted into tissue with 100 mm to 150 mm of its length, and might be used in soft tissue core biopsies in the neck, the head, the breast, the prostate, and the liver.

A fine aspiration needle of soft tissue might have an outer diameter between 0.711 mm and 2.108 mm, might be inserted into soft tissue with 100 mm to 150 mm of its length, and might be used for aspiration of soft tissue.

A brain biopsy needle might have an outer diameter of 2.108 mm, might be inserted into tissue with 150 mm up to 250 mm of its length, and might be used for diagnostic brain biopsies.

Finally, the device may include a needle electrode having an outer diameter of 2.108 mm and smaller, the electrode might be inserted into tissue up to 250 mm of its length, and might be used for radiofrequency ablation for instance of tumors.

Figure 9:
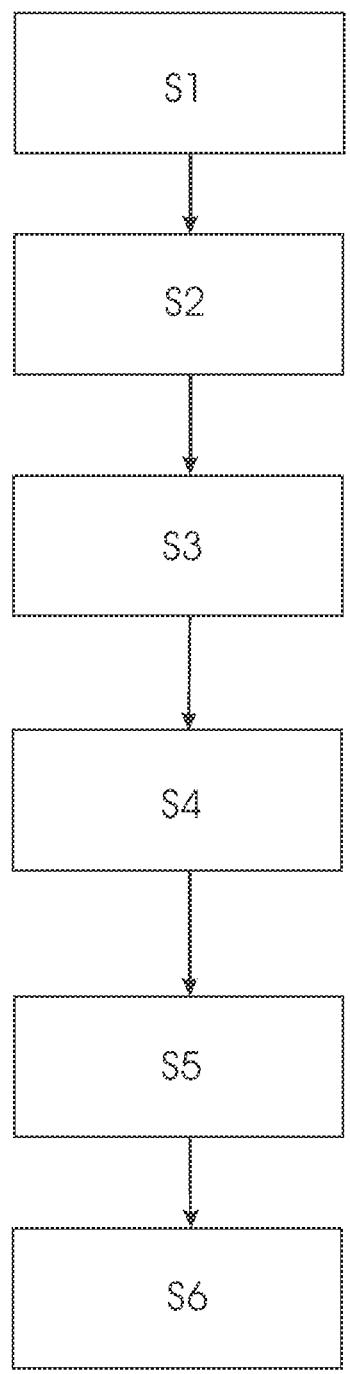
FIG. 9 is a flow chart illustrating steps of a method according to an embodiment.

The flow-chart in FIG. 9 illustrates the principle of the steps performed in accordance with an embodiment described herein. It will be understood that the steps described, are major steps, wherein these major steps might be differentiated or divided into several sub-steps. Furthermore, there might be also sub-steps between these major steps. In step S1, a photonic biopsy device is positioned within tissue of a living body. This may be performed under image guidance. Furthermore, the positioning may be controlled by means of the tissue inspection provided by the optical fibers within the biopsy device.

In step S2, when a target region for a biopsy is reached, an in-vivo tissue inspection is performed to obtain in-vivo information related to a specific tissue.

In step S3, the inspected tissue is extracted from the living body. The extraction may take place either by removing the biopsy device with the tissue sample sealed in the notch of the device, or by applying vacuum and sucking out the tissue sample through a channel provided in the biopsy device. The extracted tissue sample may then be transferred to a device for ex-vivo tissue inspection.

It is noted that sucking out the tissue sample and thus leaving the tip of the biopsy device in the target region may provide for the possibility to perform the method again in close vicinity to the former tissue inspection, if necessary. This may be decided immediately after extracting and ex-vivo inspecting the former tissue sample.

In step S4, an ex-vivo tissue inspection is performed on the previously extracted tissue sample. The step may include any necessary preparation steps like making tissue slices and staining the slices with H&E and/or with specific biomarkers. The tissue slices may also be digitized using a digital pathology system.

In step S5, the information obtained in-vivo is combined and/or integrated with the information obtained ex-vivo. This can also be molecular diagnostics data (e.g. sequencing or PCR), performed on the tissue biopsy or part of the biopsy.

In step S6, the tissue sample may be situated in a storage container to save the sample. Together with the tissue, all the obtained information may be stored at the container, for example in an electronic chip, wherein the information may include the in-vivo pathology data, the ex-vivo pathology data, the information representing the location at which the biopsy has been taken, and the like. In other words, all data received during the complete method, may be stored together with the sample in the storage container.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS

10 shaft
12 insert
13 opening
15 distal end
20 recess
30 bevel
35 fiber body
40 optical fiber
45 channel/opening
50 tubular member
55 distal edge
60 console
64 light source
66 light detector
68 monitor
70 suction device
80 device for ex-vivo tissue inspection
90 storage container
100 shaft
200 notch
500 outer member

The invention claimed is:

1. A system for obtaining pathological information, the system comprising:
   a biopsy device comprising:
     a tubular member having a distal end;
     a hollow shaft having a distal end, wherein a sidewardly facing notch is formed in the hollow shaft adjacent the distal end of the hollow shaft, wherein the hollow shaft is movably accommodated within the tubular member;
     an elongated fiber body configured to at least partially accommodate therein a plurality of optical fibers, the plurality of optical fibers having a distal end, wherein the elongated fiber body is: (i) accommodated within the hollow shaft and (ii) configured to remain at a fixed position during ejection of the hollow shaft from the distal end of the tubular member,
     wherein the tubular member is movable between a first location in which the sidewardly facing notch is covered by the tubular member, and a second location in which the sidewardly facing notch is not covered by the tubular member, and
     wherein the hollow shaft is movable between a first position in which the distal end of the plurality of optical fibers is located at a distal-most tip of the distal end of the hollow shaft with the elongated fiber body extending through the sidewardly facing notch, and a second position in which the distal end of the plurality of optical fibers is located proximally to the sidewardly facing notch; and
     an insert arranged in a fixed position within a portion of the hollow shaft between the distal end of the hollow shaft and the sidewardly facing notch, the insert configured to close the portion of the hollow shaft from entry of tissue when the hollow shaft is in the second position, the insert comprising a plurality of guiding channels configured to receive the plurality of optical fibers when the hollow shaft is in the first position.

2. The system of claim 1, wherein the elongated fiber body of the biopsy device comprises a bevel at a distal end of the elongated fiber body, with the distal end of the plurality of optical fibers located adjacent the bevel of the elongated fiber body, and wherein the bevel of the elongated fiber body is located adjacent the distal end of the hollow shaft, when the hollow shaft is in the first position.

3. The system of claim 1, wherein the biopsy device further comprises a channel for injecting or extracting a fluid.

4. The system of claim 1, wherein the sidewardly facing notch is configured to accommodate a tissue sample to be taken from a tissue.

5. The system of claim 1, further comprising a suction device for applying vacuum, wherein the biopsy device further comprises a tissue retraction channel, wherein the suction device is configured to apply the vacuum to the tissue retraction channel.

6. The system of claim 1, further comprising a console including a light source, a light detector and a processor configured to process signals provided by the light detector, the console being configured for in-vivo tissue inspection.

7. The system of claim 6, further comprising a storage container configured to receive an extracted tissue sample and store pathology information obtained by an in-vivo tissue inspection and/or an ex-vivo tissue inspection.

8. The system of claim 1, further comprising a tissue analysis processor configured to perform ex-vivo tissue inspection.

9. The system of claim 1, wherein the tubular member is configured to cut a tissue located in the sidewardly facing notch when the tubular member is moved to the first location in which the sidewardly facing notch is covered by the tubular member.

10. The system of claim 1, wherein the elongated fiber body is a solid body in which are provided a plurality of channels, and wherein the plurality of optical fibers are accommodated within the plurality of channels.

11. The system of claim 1, wherein the hollow shaft is configured to eject in length to the second position in which the elongated fiber body faces proximally to the sidewardly facing notch after the ejection.

12. A system for obtaining pathological information, the system comprising:
a biopsy device comprising:
a tubular member having a distal end;
a hollow shaft having a distal end, wherein a sidewardly facing notch is formed in the hollow shaft adjacent the distal end of the hollow shaft, wherein the hollow shaft is movably accommodated within the tubular member; and
an elongated fiber body configured to accommodate therein a plurality of optical fibers, the plurality of optical fibers having a distal end, wherein the elongated fiber body is: (i) accommodated within the hollow shaft and (ii) configured to remain at a fixed position during ejection of the hollow shaft from the distal end of the tubular member; and
a console including a light source, a light detector and a processor configured to process signals provided by the light detector, the console being configured for in-vivo tissue characterization,
wherein the tubular member is movable between a first location in which the sidewardly facing notch is covered by the tubular member, and a second location in which the notch is not covered by the tubular member,
wherein the hollow shaft is movable between a first position in which the distal end of the plurality of optical fibers is located at a distal-most tip of the distal end of the hollow shaft with the elongated fiber body extending through the sidewardly facing notch, and a second position in which the distal end of the plurality of optical fibers is located proximally to the sidewardly facing notch, and
wherein the biopsy device further comprises an insert arranged in a fixed position within a portion of the hollow shaft between the distal end of the hollow shaft and the sidewardly facing notch, the insert configured to close the portion of the hollow shaft from entry of tissue when the hollow shaft is in the second position, the insert comprising a plurality of guiding channels configured to receive the plurality of optical fibers when the hollow shaft is in the first position.

13. The system of claim 12, wherein the elongated fiber body of the biopsy device comprises a bevel at a distal end of the elongated fiber body, with the distal end of the plurality of optical fibers located adjacent the bevel of the elongated fiber body, and wherein the bevel of the elongated fiber body is located adjacent the distal end of the hollow shaft, when the hollow shaft is in the first position.

14. The system of claim 12, wherein the biopsy device further comprises a channel for injecting or extracting a fluid.

15. The system of claim 12, wherein the sidewardly facing notch is configured to accommodate a tissue sample to be taken from a tissue.

16. The system of claim 12, further comprising a suction device for applying vacuum, wherein the biopsy device further comprises a tissue retraction channel, wherein the suction device is configured to apply the vacuum to the tissue retraction channel.

17. The system of claim 12, further comprising a storage container configured to receive an extracted tissue sample and to store pathology information obtained by an in-vivo tissue inspection and/or an ex-vivo tissue inspection.

18. The system of claim 12, further comprising a tissue analysis processor configured to perform ex-vivo tissue inspection.

19. The system of claim 12, wherein the tubular member is configured to cut a tissue located in the sidewardly facing notch when the tubular member is moved to the first location in which the sidewardly facing notch is covered by the tubular member.

20. The system of claim 12, wherein the elongated fiber body is a solid body in which are provided a plurality of channels, and wherein the plurality of optical fibers are accommodated within the plurality of channels.

21. The system of claim 12, wherein the hollow shaft is configured to eject in length to the second position in which the elongated fiber body faces proximally to the sidewardly facing notch after the ejection.

* * * * *